(12) United States Patent
Achilefu et al.

(10) Patent No.: US 6,217,848 B1
(45) Date of Patent: Apr. 17, 2001

(54) CYANINE AND INDOCYANINE DYE BIOCONJUGATES FOR BIOMEDICAL APPLICATIONS

(75) Inventors: Samuel Achilefu, Bridgeton; Richard Bradley Dorshow, St. Louis; Joseph Edward Bugaj, St. Charles; Raghavan Rajagopalan, Maryland Heights, all of MO (US)

(73) Assignee: Mallinckrodt Inc., Louis, MO (US)

( * ) Notice: Subject to any disclaimer, the term of this patent is extended or adjusted under 35 U.S.C. 154(b) by 0 days.

(21) Appl. No.: 09/325,769

(22) Filed: Jun. 4, 1999

Related U.S. Application Data
(60) Provisional application No. 60/135,060, filed on May 20, 1999.

(51) Int. Cl.[7] .......................... A61K 51/00; A61M 36/14
(52) U.S. Cl. ........................ 424/9.1; 424/1.11; 424/1.65; 424/1.69; 544/3; 544/54
(58) Field of Search ................................... 424/1.11, 1.65, 424/9.1, 9.3, 9.4, 9.5, 9.6; 548/400, 452, 469, 509; 544/3, 54

(56) References Cited

U.S. PATENT DOCUMENTS
5,453,505  9/1995  Lee et al. .

FOREIGN PATENT DOCUMENTS
| | | |
|---|---|---|
| 2205906 | 6/1996 | (CA) . |
| 9617628 | 6/1996 | (WO) . |
| 9822146 | 5/1998 | (WO) . |
| 9848838 | 11/1998 | (WO) . |
| 9848846 | 11/1998 | (WO) . |

OTHER PUBLICATIONS

Becker, A., et al., "Transferrin–Mediated Tumor Delivery of Contrast Media for Optical Imaging and Magnetic Resonance Imaging", Technical Abstract Digest, International Symposium on Biomedical Optics, 23 to 29 Jan. 1999, San Jose, California, cover page and page 139, Abstract No. 3600A–36.

Brinkley, M., "A Brief Survey of Methods for Preparing Protein Conjugates with Dyes, Haptens, and Cross–Linking Reagents", Perspectives in Bioconjugate Chemistry (Ed. Claude Meares, ACS Publication, Washington, DC), pp. 59–70.

de Jong, M., et al., "Comparison of [111]In–labeled Somatostatin Analogues for Tumor Scintigraphy and Radionuclide Therapy", *Cancer Research* 1998; 58:437–441.

Jain, R., "Barriers to Drug Delivery in Solid Tumors", *Scientific American*, Jul. 1994; 271(1):58–65.

Patonay, G. and Antoine, M., "Near–Infrared Fluorogenic Labels: New Approach to an Old Problem", *Analytical Chemistry*, Mar. 15, 1991; 63(6):321A–327A.

Slavik, J., "Fluorescent Probes in Cellular and Molecular Biology", 1994, CRC Press, Inc., Boca Raton, FL; 2 cover pages, pp. 1–12.

*Primary Examiner*—Dameron L. Jones
(74) *Attorney, Agent, or Firm*—Rothwell, Figg, Ernst & Manbeck

(57) ABSTRACT

Dye-peptide conjugates useful for diagnostic imaging and therapy are disclosed. The dye-peptide conjugates include several cyanine dyes with a variety of bis- and tetrakis (carboxylic acid) homologues. The small size of the compounds allows more favorable delivery to tumor cells as compared to larger molecular weight imaging agents. The various dyes are useful over the range of 350–1300 nm, the exact range being dependent upon the particular dye. Use of dimethylsulfoxide helps to maintain the fluorescence of the compounds. The molecules of the invention are useful for diagnostic imaging and therapy, in endoscopic applications for the detection of tumors and other abnormalities and for localized therapy, for photoacoustic tumor imaging, detection and therapy, and for sonofluorescence tumor imaging, detection and therapy.

13 Claims, 10 Drawing Sheets

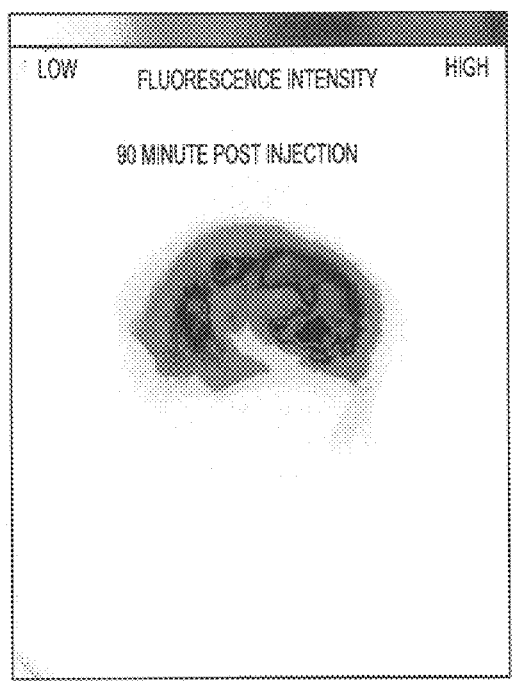 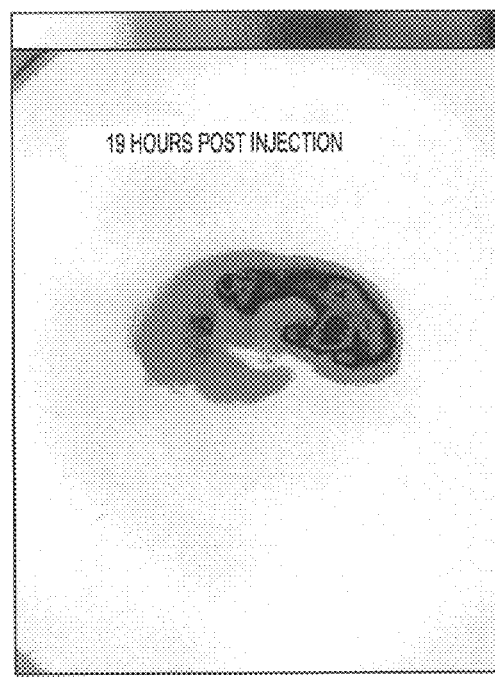
FIG. 3A
FIG. 3B

CYANINE AND INDOCYANINE DYE BIOCONJUGATES FOR BIOMEDICAL APPLICATIONS

CROSS REFERENCE TO RELATED APPLICATIONS

This application is related to U.S. Provisional Patent Application Serial No. 60/135,060 filed May 20, 1999, to which priority is claimed and which is incorporated herein by reference.

FIELD OF INVENTION

This invention relates generally to novel dye-bioconjugates for use in diagnosis and therapy. Particularly, this invention relates to novel compositions of cyanine dye bioconjugates of bioactive molecules for site-specific delivery of these agents for optical tomographic, endoscopic, photoacoustic, sonofluorescent, laser assisted guided surgery, and therapeutic purposes. More particularly, this invention relates to a method of preparation and use of cyanine dye bioconjugates for visualization and detection of tumors. This invention is also related to the method of preventing fluorescence quenching by the use of biocompatible organic solvents.

BACKGROUND OF THE INVENTION

Several dyes that absorb and emit light in the visible and near-infrared region of the electromagnetic spectrum are currently being used for various biomedical applications due to their biocompatibility, high molar absorptivity, or high fluorescence quantum yields. This high sensitivity parallels that of nuclear medicine and permits visualization of organs and tissues without the negative effect of ionizing radiation. Most dyes lack specificity for particular organs or tissues and, hence, these dyes must be attached to bioactive carriers such as proteins, peptides, carbohydrates, and the like to deliver the dyes to specific regions in the body. Several studies on the use of near infrared dyes and dye-biomolecule conjugates have been published (Patonay et al.,1991; Slavik, 1994 Brinkley, 1993; Lee and Woo, U.S. Pat. No. 5,453,505; Hohenschuh, WO 98/48846; Turner et al., WO 98/22146; Licha et al., WO 96/17628; and Snow et al., WO 98/48838). Of particular interest is the targeting of tumor cells with antibodies or other large protein carriers as delivery vehicles (Becker, et al., 1999). Such an approach has been widely used in nuclear medicine applications, and the major advantage is the retention of a carrier's tissue specificity since the molecular volume of the dye is substantially smaller than the carrier. However, this approach does have some serious limitations in that the diffusion of high molecular weight bioconjugates to tumor cells is highly unfavorable, and is further complicated by the net positive pressure in solid tumors (Jain, 1994). Furthermore, many dyes in general, and cyanine dyes, in particular, tend to form aggregates in aqueous media that lead to fluorescence quenching. Therefore, there is a need to prepare low molecular weight dye-biomolecule conjugates to enhance tumor detection, and to prepare novel dye compositions to preserve fluorescence efficiency of dye molecules.

The publications and other materials used herein to support the background of the invention or provide additional details respecting the practice, are incorporated herein by reference, and for convenience are respectively grouped in the appended List of References.

SUMMARY OF THE INVENTION

The present invention relates particularly to the novel composition comprising cyanine dye bioconjugates of general formula 1 wherein a and b vary from 0 to 5; $W^1$ and $X^1$ may be

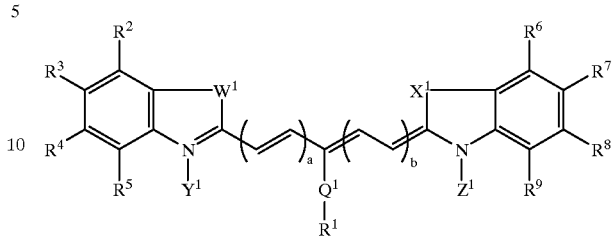

Formula 1 the same or different and are selected from the group consisting of $—CR^{10}R^{11}$, $—O—$, $—NR^{12}$, $—S—$, or $—Se$; $Q^1$ is a single bond or is selected from the group consisting of $—O—$, $—S—$, $—Se—$, and $—NR^{13}$; $R^1$, $R^{10}$ to $R^{15}$, and $R^{29}$–$R^{40}$ may be the same or different and are selected from the group consisting of hydrogen, $C_1$–$C_{10}$ alkyl, $C_1$–$C_{10}$ aryl, $C_1$–$C_{10}$ alkoxyl, $C_1$–$C_{10}$ polyalkoxyalkyl, $—CH_2(CH_2OCH_2)_c—CH_2—OH$, $C_1$–$C_{20}$ polyhydroxyalkyl, $C_1$–$C_{10}$ polyhydroxyaryl, $C_1$–$C_{10}$ aminoalkyl, $—(CH_2)_d—CO_2H$, $—(CH_2)_e—CONH-Bm$, $—CH_2—(CH_2OCH_2)_f—CH_2—CONH-Bm$, $—(CH_2)_g—NHCO-Bm$, $—CH_2—(CH_2OCH_2)_h—CH_2—NHCO-Bm$, $—(CH_2)_{yy}—OH$ or $—CH_2—(CH_2OCH_2)_{zz}—CH_2—OH$; $Y^1$ is selected from the group consisting of $—(CH_2)_i—CONH-Bm$, $—CH_2—(CH_2OCH_2)_j—CH_2—CONH-Bm$, $—(CH_2)_k—NHCO-Bm$, $—CH_2—(CH_2OCH_2)_l—CH_2—NHCO-Bm$, $—(CH_2)_m—N(R^{14})—(CH_2)_n—CONH-Bm$, $(CH_2)_{aa}—N(R^{29})—(CH_2)_{bb}—NHCO-Bm$, $—(CH_2)_p—N(R^{15})—CH_2—(CH_2OCH_2)_q—CH_2—CONH-Bm$, $—(CH_2)_{cc}—N(R^{30})—CH_2—(CH_2OCH_2)_{dd}—CH_2—NHCO-Bm$, $—CH_2—(CH_2OCH_2)_{ee}—CH_2—N(R^{31})—(CH_2)_{ff}—CONH-Bm$, $—CH_2—(CH_2OCH_2)_{gg}—CH_2—N(R^{32})—(CH_2)_{hh}—NHCO-Bm$, $—CH_2—(CH_2OCH_2)_{ii}—CH_2—N(R^{33})—CH_2—(CH_2OCH_2)_{jj}—CH_2—CONH-Bm$ or $—CH_2—(CH_2OCH_2)_{kk}—CH_2—N(R^{34})—CH_2—(CH_2OCH_2)_{ll}—CH_2—NHCO-Bm$; d, e, g, i, k, m, n, p, aa, bb, cc, ff, hh and yy vary from 1 to 10; c, f, h, j, l, q, dd, ee, gg, ii, jj, kk, ll and zz vary from 1 to 100; Bm is any bioactive peptide, protein, cell, oligosaccharide, glycopeptide, peptidomimetic, drug, drug mimic, hormone, metal chelating agent, radioactive or nonradioactive metal complex, or echogenic agent; $Z^1$ is selected from the group consisting of $—(CH_2)_r—CO_2H$, $—(CH_2)_t—OH$, $—(CH_2)_r—NH_2$, $—CH_2—(CH_2OCH_2)_s—CH_2—CO_2H$, $—CH_2—(CH_2OCH_2)_s—CH_2—OH$, $—CH_2—(CH_2OCH_2)_s—CH_2—NH_2$, $—(CH_2)_t—CONH-Dm$, $—CH_2—(CH_2OCH_2)_u—CH_2—CONH-Dm$, $—(CH_2)_v—NHCO-Dm$, $—CH_2—(CH_2OCH_2)_o—CH_2—NHCO-Dm$, $—(CH_2)_w—N(R^{14})—(CH_2)_x—CONH-Dm$, $(CH_2)_{mm}—N(R^{35})—(CH_2)_{nn}—NHCO-Dm$, $—(CH_2)_y—N(R^{15})—CH_2—(CH_2OCH_2)_z—CH_2—CONH-Dm$, $—(CH_2)_{uu}—N(R^{39})—CH_2—(CH_2OCH_2)_{vv}—CH_2—NHCO-Dm$, $—CH_2—(CH_2OCH_2)_{ww}—CH_2—N(R^{40})—(CH_2)_{xx}—CONH-Dm$, $—CH_2—(CH_2OCH_2)_{oo}—CH_2—N(R^{36})—(CH_2)_{pp}—NHCO-Dm$, $—CH_2—(CH_2OCH_2)_{qq}—CH_2—N(R^{37})—CH_2—(CH_2OCH_2)_{rr}—CH_2—CONH-Dm$ or $—CH_2—(CH_2OCH_2)_{ss}—CH_2—N(R^{38})—CH_2—(CH_2OCH_2)_{tt}—CH_2—NHCO-Dm$; r, t, v, w, x, y, mm, nn, pp, uu and xx vary from 1 to 10, and o, s, u, z, oo, qq, rr, ss, tt, vv and ww vary from 1 to 100; and Dm is any bioactive peptide, antibody, antibody fragment, oligosaccharide, drug, drug mimic, glycomimetic, glycopeptide, peptidomimetic, hormone, and the like; $R^2$ to $R^9$ may be the same or different and are selected from the group consisting of hydrogen, $C_1-C_{10}$ alkyl, $C_1-C_{10}$ aryl, hydroxyl, $C_1-C_{10}$ polyhydroxyalkyl, $C_1-C_{10}$ alkoxyl, amino, $C_1-C_{10}$ aminoalkyl, cyano, nitro, or halogen.

The present invention also relates to the novel composition comprising cyanine dye bioconjugates of general formula 2 wherein a' and b' are defined in the same manner as a and b; $W^2$ and $X^2$ are defined in the same manner $W^1$ and $X^1$; $Q^2$ is defined in the same manner as $Q^1$; $R^{16}$ is defined in the same manner as $R^1$; $Y^2$ is defined in the same manner as $Y^1$; $Z^2$ is defined in the same manner as $Z^1$; and $R^{17}$ to $R^{28}$ are defined in the same manner as $R^2$.

This invention is also related to the method of preventing fluorescence quenching. It is known that cyanine dyes generally form aggregates in aqueous media leading to fluorescence quenching. This problem is further accentuated by the conjugation of large hydrophobic dyes to small molecular peptides. We observed that the addition of a biocompatible organic solvent such as 1–50% dimethylsulfoxide (DMSO) restored the fluorescence by preventing aggregation and allowed the visualization of tumors.

Formula 2

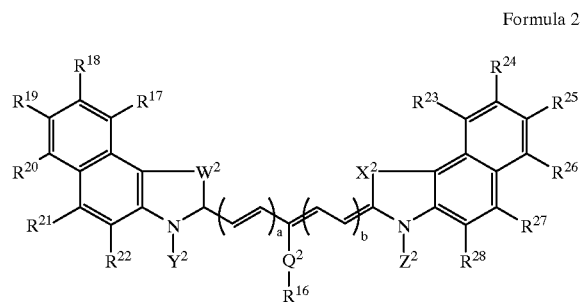

In one embodiment of the invention, the dye-peptide conjugates are useful for optical tomographic, endoscopic, photoacoustic and sonofluorescent applications for the detection and treatment of tumors and other abnormalities.

In another aspect of the invention, the dye-peptide conjugates of the invention are useful for localized therapy.

In yet another aspect of the invention, the dye peptide conjugates of the invention are useful for the detection of the presence of tumors and other abnormalities by monitoring the blood clearance profile of the conjugates.

In a further embodiment of the invention, the dye-peptide conjugates are useful for laser assisted guided surgery for the detection of small micrometastases of, e.g., somatostatin subtype 2 (SST-2) positive, tumors upon laparoscopy.

In yet another aspect of the invention, the dye-peptide conjugates of this invention are useful for diagnosis of atherosclerotic plaques and blood clots.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIGS. 1A–B are images of a rat with an induced pancreatic ductal adenocarcinoma tumor (DSL 6A) imaged at 2 minutes (FIG. 1A) and 30 minutes (FIG. 1B) post injection. FIGS. 1C–D are images of a rat with an induced prostatic carcinoma tumor (R3327-H) imaged at 2 minutes (FIG. 1C) and 30 minutes (FIG. 1D) post injection. FIGS. 1E–F are images of a rat with an induced pancreatic acinar carcinoma (CA20948) expressing the SST-2 receptor imaged at 2 minutes (FIG. 1E) and 30 minutes (FIG. 1F) post injection.

FIGS. 3A–B show images of rats with the pancreatic acinar carcinoma (CA20948) 90 minutes (FIG. 3A) and 19 hours (FIG. 3B) post injection of Cytate 1.

FIG. 11 shows scheme 1 for preparing bis-carboxylates.

FIG. 12 shows scheme 2 for preparing tetra-carboxylates.

FIG. 13 shows scheme 3 for preparing bioconjugates.

DETAILED DESCRIPTION OF THE INVENTION

Figure 1A:
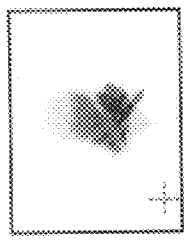
FIGS. 1A–F represent images at 2 minutes and 30 minutes post injection of indocyanine green into rats with various tumors.

The novel bioconjugates of the present invention exploit the symmetric nature of the cyanine and indocyanine dye structures by incorporating one to ten receptor targeting groups, in close proximity to each other such that the receptor binding can be greatly enhanced due to a cooperative effect. Accordingly, several cyanine dyes containing one or more targeting domains have been prepared and tested in vivo for biological activity.

The novel compositions of the present invention comprise dye-bioconjugates of formulas 1 and 2 and offer significant advantages over those currently described in the art. They are applicable to various biomedical applications including, but not limited to, tomographic imaging of organs; monitoring of organ functions; coronary angiography; fluorescence endoscopy; detection, imaging, and therapy of tumors; laser guided surgery, photoacoustic and sonofluorescent methods; and the like. Specific embodiments to accomplish some of the aforementioned biomedical applications are given below. The bioconjugates are prepared by the methods well known in the art and are shown in FIGS. 1–3 which are illustrated in FIGS. 11–13.

In a preferred embodiment, the bioconjugates according to the present invention have the general formula 1 wherein a and b vary from 0 to 3; $Q^1$ is a single bond; $R^1$ to $R^9$ are hydrogens; $W^1$ and $X^1$ are —$CR^{10}R^{11}$; $Y^1$ is —$(CH_2)_i$—CONH-Bm, —$(CH_2)_k$—NHCO-Bm, or —$(CH_2)_m$—N($R^{14}$)—$(CH_2)_n$—CONH-Bm; $Z^1$ is —$(CH_2)_r$—OH, —$(CH_2)_r$—$CO_2H$, —$(CH_2)_r$—$NH_2$, —$(CH_2)_t$—CONH-Dm, —$(CH_2)_v$—NHCO-Dm, —$(CH_2)_w$—N($R^{14}$)—$(CH_2)_x$—CONH-Dm,—$CH_2$—$(CH_2OCH_2)_s$—$CH_2$—OH,—

$CH_2—(CH_2OCH_2)_s—CH_2—CO_2H$, $—CH_2—(CH_2OCH_2)_s$ —$CH_2—NH_2$, $—CH_2—(CH_2OCH_2)_u—CH_2—CONH\text{-}Dm$, $—CH_2—(CH_2OCH_2)_o—CH_2—NHCO\text{-}Dm$, or $—CH_2—(CH_2OCH_2)_{ww}—CH_2—N(R^{40})—(CH_2)_{xx}—CONH\text{-}Dm$; and Bm is a tumor specific biomolecule or drug mimic selected from the group consisting of peptides or oligosaccharides containing 2–50 monomer units and including somatostatin, bombesin, neurotensin, cholecystokinin and vasoactive intestinal polypeptide.

In another preferred embodiment, the bioconjugates according to the present invention have the general formula 1 wherein a and b are 3; $Q^1$ is a single bond; $R^1$ to $R^9$ are hydrogens; $W^1$ and $X^1$ are $—C(CH_3)_2$; $Y^1$ is $—(CH_2)_i—CONH\text{-}Bm$ or $—CH_2—(CH_2OCH_2)_i—CH_2—CONH\text{-}Bm$ wherein i varies from 1 to 4; and $Z^1$ is $—(CH_2)_r—CO_2H$, $—(CH_2)_t—CONH\text{-}Dm$, $—CH_2—(CH_2OCH_2)_s—CH_2—CO_2H$ or $—CH_2—(CH_2OCH_2)_u—CH_2—CONH\text{-}Dm$, wherein r and t vary from 1–4; and Bm is a tumor specific biomolecule selected from the group consisting of Octreotate and its mimics, Octreotide derivatives and their mimics, bombesin analogs, cholecystokinin analogs, and neurotensin analogs.

In another preferred embodiment, the bioconjugates according to the present invention have the general formula 2 wherein a' and b' vary from 0 to 3; $Q^2$ is a single bond; $R^{16}$ to $R^{28}$ are hydrogens; $W^2$ and $X^2$ are $—CR^{10}R^{11}$; $Y^2$ is $—(CH_2)_i—CONH\text{-}Bm$, $—(CH_2)_k—NHCO\text{-}Bm$, or $—(CH_2)_m—N(R^{14})—(CH_2)_n—CONH\text{-}Bm$; $Z^2$ is $—(CH_2)_r—CO_2H$, $—(CH_2)_r—NH_2$, $—(CH_2)_r—OH$, $—(CH_2)_t—CONH\text{-}Dm$, $—(CH_2)_v—NHCO\text{-}Dm$, $—(CH_2)_w—N(R^{14})—(CH_2)_x—CONH\text{-}Dm$, $—CH_2—(CH_2OCH_2)_s—CH_2—CO_2H$, $—CH_2—(CH_2OCH_2)_s—CH_2—NH_2$, $—CH_2—(CH_2OCH_2)_s—CH_2—OH$, $—CH_2—(CH_2OCH_2)_u—CH_2—CONH\text{-}Dm$, $—CH_2—(CH_2OCH_2)_o—CH_2—NHCO\text{-}Dm$, $—CH_2—(CH_2OCH_2)_{ww}—CH_2—N(R^{40})—(CH_2)_{xx}—CONH\text{-}Dm$; and Bm is a tumor specific biomolecule or drug mimic selected from the group consisting of peptides and oligosaccharides containing 2–50 monomer units.

In another preferred embodiment, the bioconjugates according to the present invention have the general formula 2 wherein a' and b' are 3; $Q^2$ is a single bond; $R^{16}$ to $R^{28}$ are hydrogens; $W^2$ and $X^2$ are $—C(CH_3)_2$; $Y^2$ is $—(CH_2)_i—CONH\text{-}Bm$ or $—CH_2—(CH_2OCH_2)_i—CH_2—CONH\text{-}Bm$ wherein i varies from 1 to 4; and $Z^2$ is $—(CH_2)_r—CO_2H$, $—(CH_2)_t—CONH\text{-}Dm$, $—CH_2—(CH_2OCH_2)_s—CH_2—CO_2H$ or $—CH_2—(CH_2OCH_2)_u—CH_2—CONH\text{-}Dm$, wherein r and t vary from 1–4; and Bm is a tumor specific biomolecule selected from the group consisting of Octreotate derivatives and their mimics, Octreotide derivatives and their mimics, bombesin analogs and their mimics, cholecystokinin analogs and their mimics, and neurotensin analogs and their mimics.

In a preferred embodiment, the methods utilize light of a wavelength in the region of 350–1300 nm.

In a preferred embodiment, a therapeutic procedure comprises attaching a porphyrin to a bioconjugate and using it for photodynamic therapy or shining light of a specific wavelength on the dipeptide conjugate of this invention to achieve a photodynamic therapy effect.

The compositions of the invention can be formulated into diagnostic compositions for enteral or parenteral administration. These compositions contain an effective amount of the dye along with conventional pharmaceutical carriers and excipients appropriate for the type of administration contemplated. For example, parenteral formulations advantageously contain a sterile aqueous solution or suspension of dye according to this invention. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids which include an effective amount of the dye in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues which are the subject of the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure.

A combination of the above represents an important approach to the use of small molecular targeting groups to image tumors by the optical methods. The present invention is further detailed in the following Examples, which are offered by way of illustration and are not intended to limit the invention in any manner. Standard techniques well known in the art or the techniques specifically described below are utilized.

EXAMPLE 1

Synthesis of Bisethylcarboxymethylindocyanine Dye (FIG. 11, $R_1$, $R_2$=fused phenyl; A=$CH_2$, n=1 and R=R'=$CO_2H$)

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 mL) was heated at 110° C. for 12 hours. The solution was cooled to room temperature and the red residue obtained was filtered and washed with acetonitrile:diethyl ether (1:1) mixture. The solid obtained was dried under vacuum to give 10 g (64%) of light brown powder. A portion of this solid (6.0 g; 16.56 mmoles), glutaconaldehyde dianil monohydrochloride (2.36 g, 8.28 mmoles) and sodium acetate trihydrate (2.93 g, 21.53 mmoles) in ethanol (150 mL) were refluxed for 90 minutes. After evaporating the solvent, 40 mL of a 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain 2 g of dark green flakes. The purity of the compound was established with $^1$H-NMR and LC-Mass spectrometry.

EXAMPLE 2

Synthesis of Bispentylcarboxymethylindocyanine Dye (FIG. 11, $R_1$, $R_2$=fused phenyl; A=$CH_2$, n=4 and R=R'=$CO_2H$)

A mixture of 1,1,2-trimethyl-[1H]-benz[e]indole (20 g, 95.6 mmoles) and 6-bromohexanoic acid (28.1 g, 144.1 mmoles) in 1,2-dichlorobenzene (250 mL) was heated at 110° C. for 12 hours. The green solution was cooled to room temperature and the brown solid precipitate formed was collected by filtration. After washing the solid with 1,2-dichlorobenzene and diethyl ether, the brown powder obtained (24 g, 64%) was dried under vacuum at room temperature. A portion of this solid (4.0 g; 9.8 mmoles), glutaconaldehyde dianil monohydrochloride (1.4 g, 5 mmoles) and sodium acetate trihydrate (1.8 g, 12.9 mmoles) in ethanol (80 mL) were refluxed for 1 hour. After evaporating the solvent, 20 mL of a 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain about 2 g of dark green flakes. The purity of the compound was established with $^1$H-NMR and LC-Mass spectrometry.

EXAMPLE 3

Synthesis of Bisethylcarboxymethylindocyanine Dye (FIG. 11, $R_1$, $R_2$=fused phenyl; A=CH$_2$, n=1 and R=R'=CO$_2$H)

This compound was prepared as described in Example 1 except that 1,1,2-trimethylindole was used as the starting material.

EXAMPLE 4

Synthesis of Bishexaethyleneglycolcarboxymethylindocyanine Dye (FIG. 11, $R_1$, $R_2$=fused phenyl; A=CH$_2$OCH$_2$, n=6 and R=R'=CO$_2$H)

This compound was prepared as described in Example 1 except that ω-bromohexaoxyethyleneglycolpropanoic acid was used in place of bromopropanoic acid and the reaction was carried out in 1,2-dimethoxypropane.

EXAMPLE 5

Synthesis of Bisethylcarboxymethylindocyanine Dye (FIG. 11, $R_1$, $R_2$=fused phenyl; A=CH$_2$, and n=1)

This compound is readily prepared as described in Example 1 except that 3-bromo-1-(N,N-bis-carboxymethyl) aminopropane is used in place of bromopropanoic acid.

EXAMPLE 6

Synthesis of Peptides

The procedure described below is for the synthesis of Octreotate. Other peptides of this invention were prepared by a similar procedure with slight modifications in some cases.

The octapeptide was prepared by an automated fluorenylmethoxycarbonyl (Fmoc) solid phase peptide synthesis using a commercial peptide synthesizer from Applied Biosystems (Model 432A SYNERGY Peptide Synthesizer). The first peptide cartridge contained Wang resin pre-loaded with Fmoc-Thr on 25 lmole scale. Subsequent cartridges contained Fmoc-protected amino acids with side chain protecting groups for the following amino acids: Cys(Acm), Thr (t-Bu), Lys(Boc), Trp(Boc) and Tyr(t-Bu). The amino acid cartridges were placed on the peptide synthesizer and the product was synthesized from the C- to the N-terminal position. The coupling reaction was carried out with 75 Emoles of the protected amino acids in the presence of 2-(1H-benzotriazol-1-yl)-1,1,3,3-tetramethyluronium hexafluorophosphate (HBTU)/N-hydroxybenzotriazole (HOBt). The Fmoc protecting group was removed with 20% piperidine in dimethylformamide. After the synthesis was complete, the thiol group was cyclized with thallium trifluoroacetate and the product was cleaved from the solid support with a cleavage mixture containing trifluoroacetic acid (85%):water (5%):phenol (5%):thioanisole (5%) for 6 hours. The peptide was precipitated with t-butyl methyl ether and lyophilized with water:acetonitrile (2:3) mixture. The peptide was purified by HPLC and analyzed with LC/MS. The amino acid sequence of Octreotate is: D-Phe-Cys'-Tyr-D-Trp-Lys-Thr-Cys'-Thr (SEQ ID NO:1), wherein Cys' indicates the presence of an intramolecular disulfide bond between two cysteine amino acids.

Octreotide was prepared by the same procedure: D-Phe-Cys'-Tyr-D-Trp-Lys-Thr-Cys'-Thr-OH (SEQ ID NO:2), wherein Cys' indicates the presence of an intramolecular disulfide bond between two cysteine amino acids.

Bombesin analogs were prepared by the same procedure except that cyclization with thallium trifluoroacetate was not needed. Side-chain deprotection and cleavage from the resin was carried out with 50 μL each of ethanedithiol, thioanisole and water, and 850 μL of trifluoroacetic acid. Two analogues were prepared: Gly-Ser-Gly-Gln-Trp-Ala-Val-Gly-His-Leu-Met-NH$_2$ (SEQ ID NO:3) and Gly-Asp-Gly-Gln-Trp-Ala-Val-Gly-His-Leu-Met-NH$_2$ (SEQ ID NO:4).

Cholecystokinin octapeptide analogs were prepared as described for Octreotate without the cyclization step. Three analogs were prepared: Asp-Tyr-Met-Gly-Trp-Met-Asp-Phe-NH$_2$ (SEQ ID NO:5); Asp-Tyr-Nle-Gly-Trp-Nle-Asp-Phe-NH$_2$ (SEQ ID NO:6); and D-Asp-Tyr-Nle-Gly-Trp-Nle-Asp-Phe-NH$_2$ (SEQ ID NO:7) wherein Nle is norleucine.

Neurotensin analog was prepared as described for Octreotate without the cyclization step: D-Lys-Pro-Arg-Arg-Pro-Tyr-Ile-Leu (SEQ ID NO:8).

EXAMPLE 7

Synthesis of Peptide-Dye Conjugates

The method described below is for the synthesis of Octreotate conjugates but a similar procedure is used for the synthesis of other peptide-dye conjugates.

The Octreotate was prepared as described in Example 6 but the peptide was not cleaved from the solid support and the N-terminal Fmoc group of Phe was retained. The thiol group was cyclized with thallium trifluoroacetate and the Phe was deprotected to liberate the free amine. Bisethylcarboxymethylindocyanine dye (53 mg, 75 μmoles) was added to an activation reagent consisting of a 0.2 M solution of HBTU/HOBt in DMSO (375 μL), and 0.2 M solution of diisopropylethylamine in DMSO (375 μL). The activation was complete in about 30 minutes and the resin-bound peptide (25 μmoles) was added to the dye. The coupling reaction was carried out at room temperature for 3 hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 5% water, 5% thioanisole and 5% phenol. The resin was filtered and cold t-butyl methyl ether (MTBE) was used to precipitate the dye-peptide conjugate which was dissolved in acetonitrile:water (2:3) mixture and lyophilized. The product was purified by HPLC to give the monoOctreotate-Bisethylcarboxymethylindocyanine dye (Cytate 1, 80%) and the bisOctreotate-Bisethylcarboxymethylindocyanine dye (Cytate 2, 20%). The monoOctreotate conjugate can be obtained almost exclusively (>95%) over the bis conjugate by reducing the reaction time to 2 hours. However, this also leads to incomplete reaction and the free Octreotate must be carefully separated from the dye conjugate in order to avoid saturation of the receptors by the non-dye conjugated peptide.

Octreotate-bispentylcarboxymethylindocyanine dye was prepared as described above with some modifications. Bispentylcarboxymethylindocyanine dye (60 mg, 75 $\mu$moles) was added to an activation reagent consisting of a 0.2 M solution of HBTU/HOBt in DMSO (400 $\mu$L), and 0.2 M solution of diisopropylethylamine in DMSO (400 $\mu$L). The activation was complete in about 30 minutes and the resin-bound peptide (25 $\mu$moles) was added to the dye. The reaction was carried out at room temperature for 3 hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 5% water, 5% thioanisole and 5% phenol. The resin was filtered and cold t-butyl methyl ether (MTBE) was used to precipitate the dye-peptide conjugate which was dissolved in acetonitrile:water (2:3) mixture and lyophilized. The product was purified by HPLC to give Octreotate-1,1,2-trimethyl-[1H]-benz[e]indole propanoic acid conjugate (10%), monoOctreotate-bispentylcarboxymethylindocyanine dye (Cytate 3, 60%) and bisOctreotate-bispentylcarboxymethylindocyanine dye (Cytate 4, 30%).

EXAMPLE 8

Formulation of peptide-dye conjugates in dimethyl sulfoxide (DMSO)

The dye-peptide conjugates are sparingly soluble in water and require the addition of solubilizing agents or co-solvents. Addition of 1–20% aqueous ethanol to the conjugates partially quenched the fluorescence intensity in vitro and the fluorescence was completely quenched in vivo (the conjugate was not detected by the CCD camera). Addition of 1–50% of DMSO either re-established or increased the fluorescence intensity of the conjugates in vitro and in vivo. The dye fluorescence remained intense for over one week. The DMSO formulations were well tolerated by experimental animals used for this invention.

EXAMPLE 9

Imaging of pancreatic ductal adenocarcinoma (DSL 6A) with Indocyanine Green (ICG)

A non-invasive in vivo fluorescence imaging apparatus was employed to assess the efficacy of contrast agents developed for tumor detection in animal models. A Laser-Max Inc. laser diode of nominal wavelength 780 nm and nominal power of 40 mW was used. The detector was a Princeton Instruments model RTE/CCD-1317-K/2 CCD camera with a Rodenstock 10 mm F2 lens (stock #542.032.002.20) attached. An 830 nm interference lens (CVI Laser Corp., part # F10-830-4-2) was mounted in front of the CCD input lens such that only emitted fluorescent light from the contrast agent was imaged. Typically, an image of the animal was taken pre-injection of contrast agent. This image was subsequently subtracted (pixel by pixel) from the post injection images. However, the background subtraction was never done once the animal had been removed from the sample area and returned at a later time for images taken several hours post injection.

DSL 6A tumors were induced in male Lewis rats in the left flank area by the introduction of material from a solid (donor) implant and the tumors were palpable in approximately 14 days.

Figure 1B:
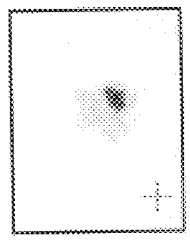

The animals were anesthetized with rat cocktail (xylazine; ketamine; acepromazine 1.5: 1.5: 0.5) at 0.8 mL/kg via intramuscular injection. The area of the tumor (left flank) was shaved to expose tumor and surrounding surface area. A 21 gauge butterfly equipped with a stopcock and two syringes containing heparinized saline was placed into the later tail vein of the rat. Patency of the vein was checked prior to administration of the ICG via the butterfly apparatus. Each animal received 500 $\mu$L of a 0.42 mg/mL solution of ICG in water. The images obtained at 2 and 30 minutes post injection are shown in FIGS. 1A–B.

EXAMPLE 10

Imaging of Prostatic Carcinoma (R3327-H) with Indocyanine Green (ICG)

Figure 1C:
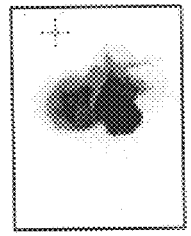
Figure 1D:
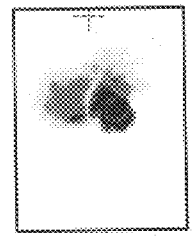

The imaging apparatus and the procedure used are described in Example 9. R3327-H tumors were induced in young male Copenhagen rats in the left flank area from a solid implant. These tumors grow very slowly and palpable masses were present 4–5 months post implant. The images obtained at 2 and 30 minutes post injection are shown in FIGS. 1C–D.

EXAMPLE 11

Imaging of Rat Pancreatic Acinar Carcinoma (CA20948) with Indocyanine Green (ICG)

Figure 1E:
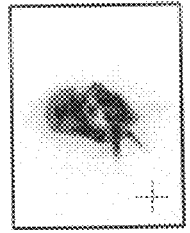
Figure 1F:
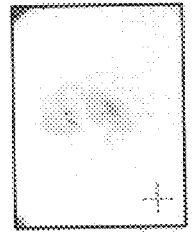

The imaging apparatus and the procedure used are described in Example 9. Rat pancreatic acinar carcinoma expressing the SST-2 receptor (CA20948) were induced by solid implant technique in the left flank area and palpable masses were detected 9 days post implant. The images obtained at 2 and 30 minutes post injection are shown in FIGS. 1E–F.

EXAMPLE 12

Imaging of Rat Pancreatic Acinar Carcinoma (CA20948) with Cytate 1

Figure 2A:
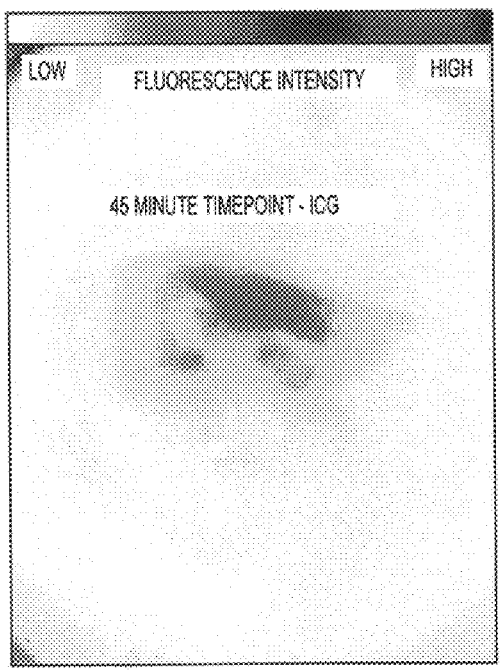
FIGS. 2A–B show a comparison of the uptake of indocyanine green and Cytate 1 at 45 minutes post injection in rats with the pancreatic acinar carcinoma (CA20948).
Figure 2B:
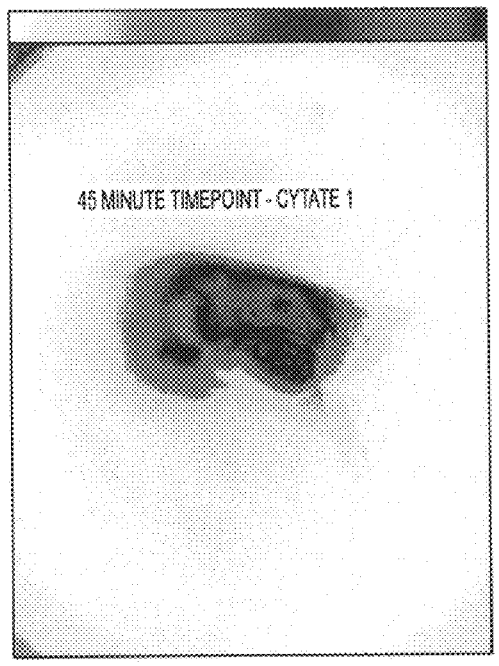

The imaging apparatus and the procedure used are described in Example 9 except that each animal received 500 $\mu$L of a 1.0 mg/mL solution of Cytate 1 solution of 25% dimethylsulfoxide in water. Rat pancreatic acinar carcinoma expressing the SST-2 receptor (CA20948) were induced by solid implant technique in the left flank area and palpable masses were detected 24 days post implant. Images were obtained at various times post injection. Uptake into the tumor was seen at 2 minutes but was not maximal until about 5 minutes. FIGS. 2A–B show a comparison of the uptake of ICG and Cytate 1 at 45 minutes in rats with the CA20948 tumor cell line. By 45 minutes the ICG has mostly cleared (FIG. 2A) whereas the Cytate 1 is still quite intense (FIG. 2B). This dye fluorescence remained intense in the tumor for several hours post-injection.

EXAMPLE 13

Imaging of Rat Pancreatic Acinar Carcinoma (CA20948) with Cytate 1 Compared with Imaging with ICG Using indocyanine green (ICG), three different tumor lines were imaged optically using a CCD camera apparatus.

Two of the lines, DSL 6/A (pancreatic) and Dunning R3327-H (prostate) indicated slow perfusion of the agent over time into the tumor and reasonable images were obtained for each. The third line, CA20948 (pancreatic), indicated only a slight but transient perfusion that was absent after only 30 minutes post injection. This indicates no non-specific localization of ICG into this line compared to the other two tumor lines suggesting a vastly different vascular architecture for this type of tumor (see FIGS. 1A–F). The first two tumor lines (DSL 6/A and R3327-H) are not as highly vascularized as CA20948 which is also rich in somatostatin (SST-2) receptors. Consequently, the detection and retention of a dye in this tumor model is an important index of receptor-mediated specificity.

Figure 4A:
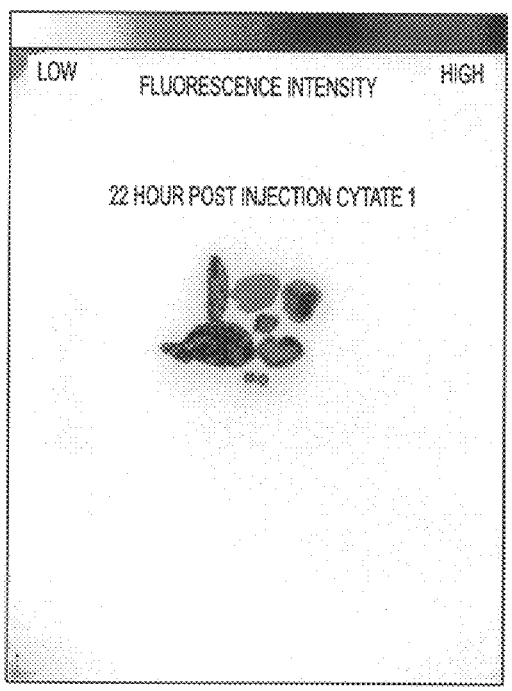
FIGS. 4A–B show images comparing selected tissue parts of a rat with the pancreatic acinar carcinoma (CA20948) 22 hours post injection with Cytate 1 (FIG. 4A) and the same tissue parts imaged in an uninjected rat (FIG. 4B).
Figure 4B:
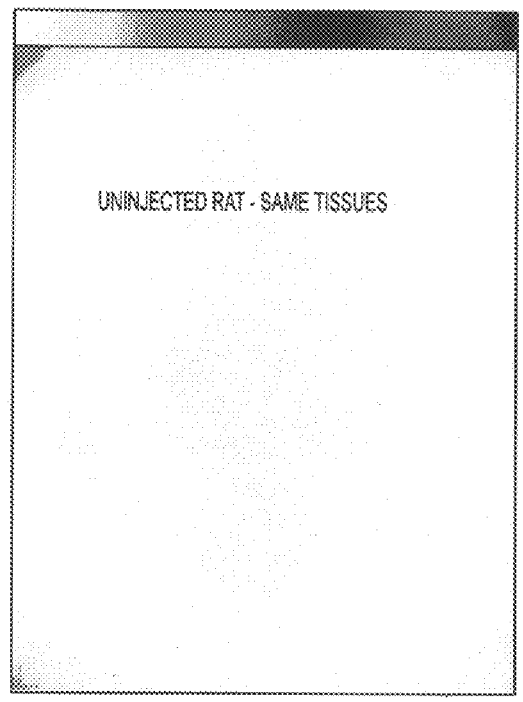

Octreotate is known to target somatostatin (SST-2) receptors, hence, we prepared cyano-Octreotates (Cytate 1 and Cytate 2). Cytate 1 was evaluated in the CA20948 Lewis rat model. Using the CCD camera apparatus strong localization of this dye was observed in the tumor at 90 minutes post injection (FIG. 3A). At 19 hours post injection the animal was again imaged (FIG. 3B) and tumor visualization was easily observed showing specificity of this agent for the SST-2 receptors present in this tumor line. As a control, the organs were imaged again (FIG. 4A) and the image was compared with that of the same tissues in the uninjected rat (FIG. 4B).

Figure 5:
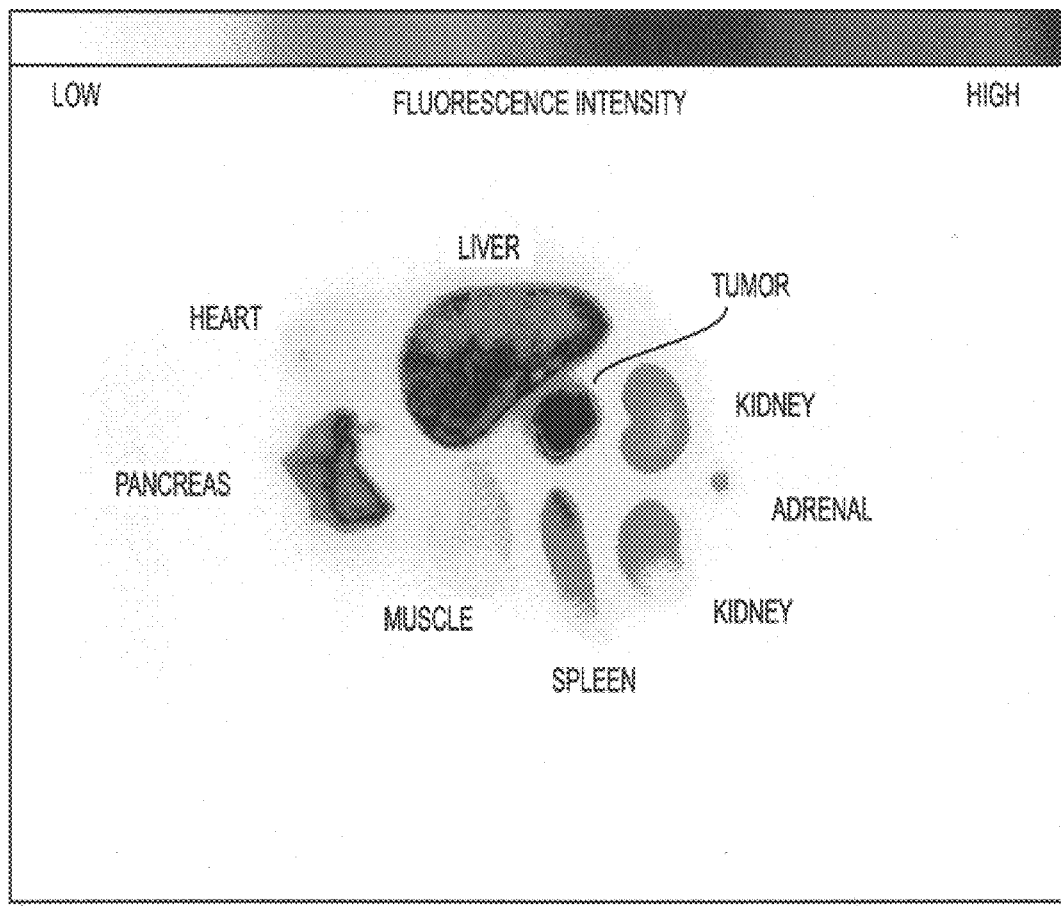
FIG. 5 is an image of individual organs taken from a rat with pancreatic acinar carcinoma (CA20948) about 24 hours after injection with Cytate 1.
Figure 6:
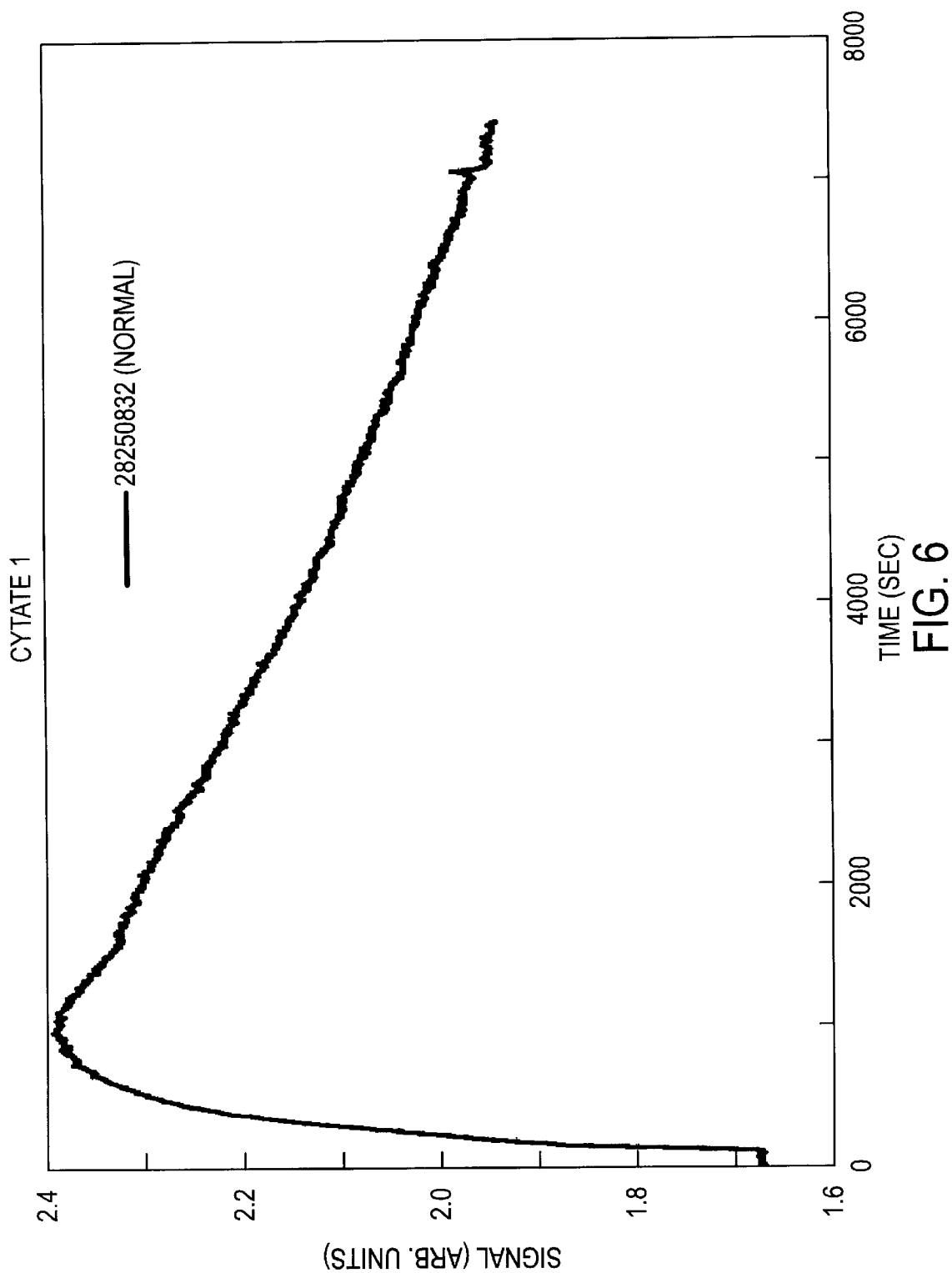
FIG. 6 is the clearance profile of Cytate 1 from the blood of a normal rat monitored at 830 nm after excitation at 780 nm.
Figure 7:
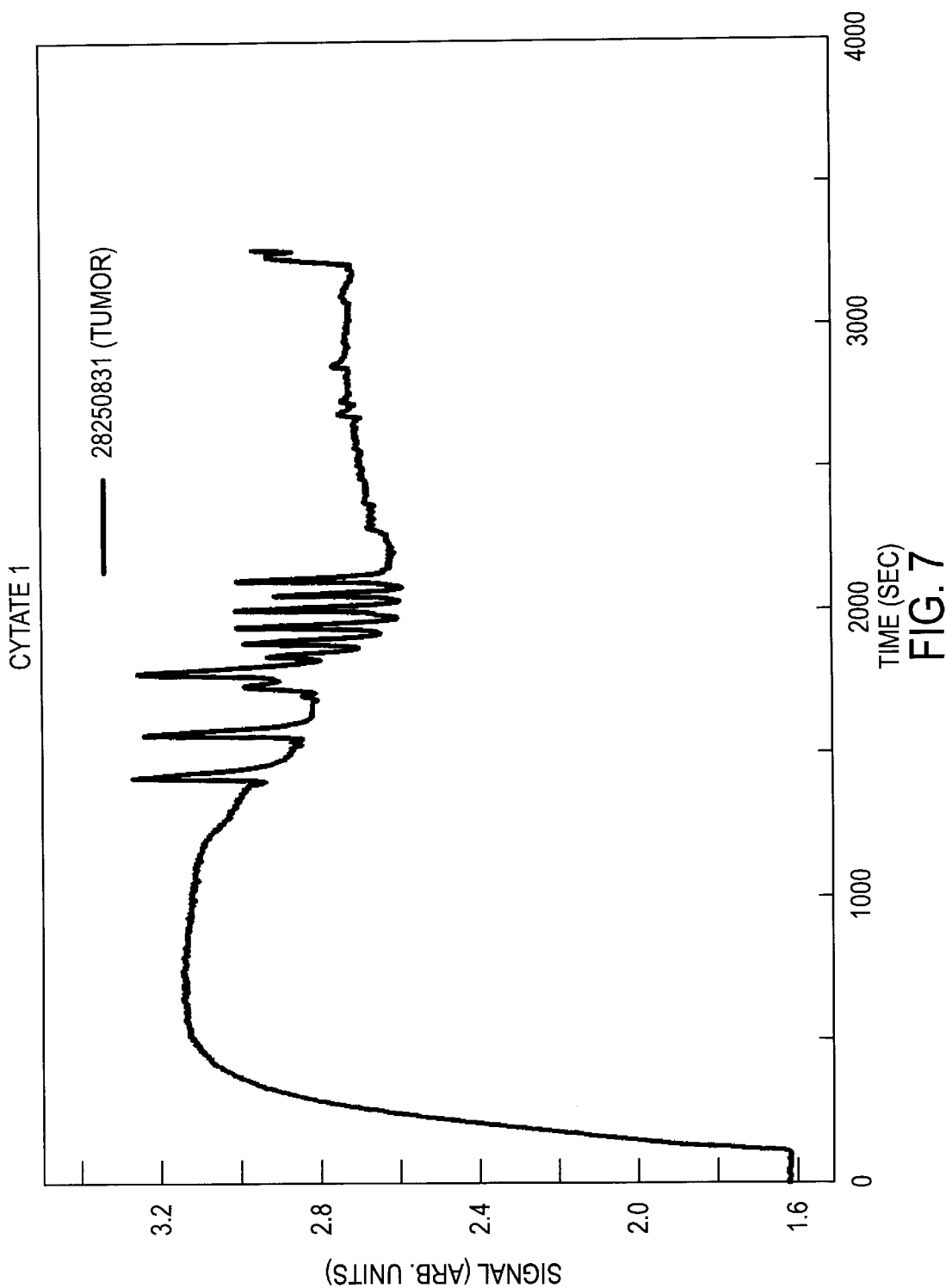
FIG. 7 is the clearance profile of Cytate 1 from the blood of a CA20948 tumored rat monitored at 830 nm after excitation at 780 nm.
Figure 8:
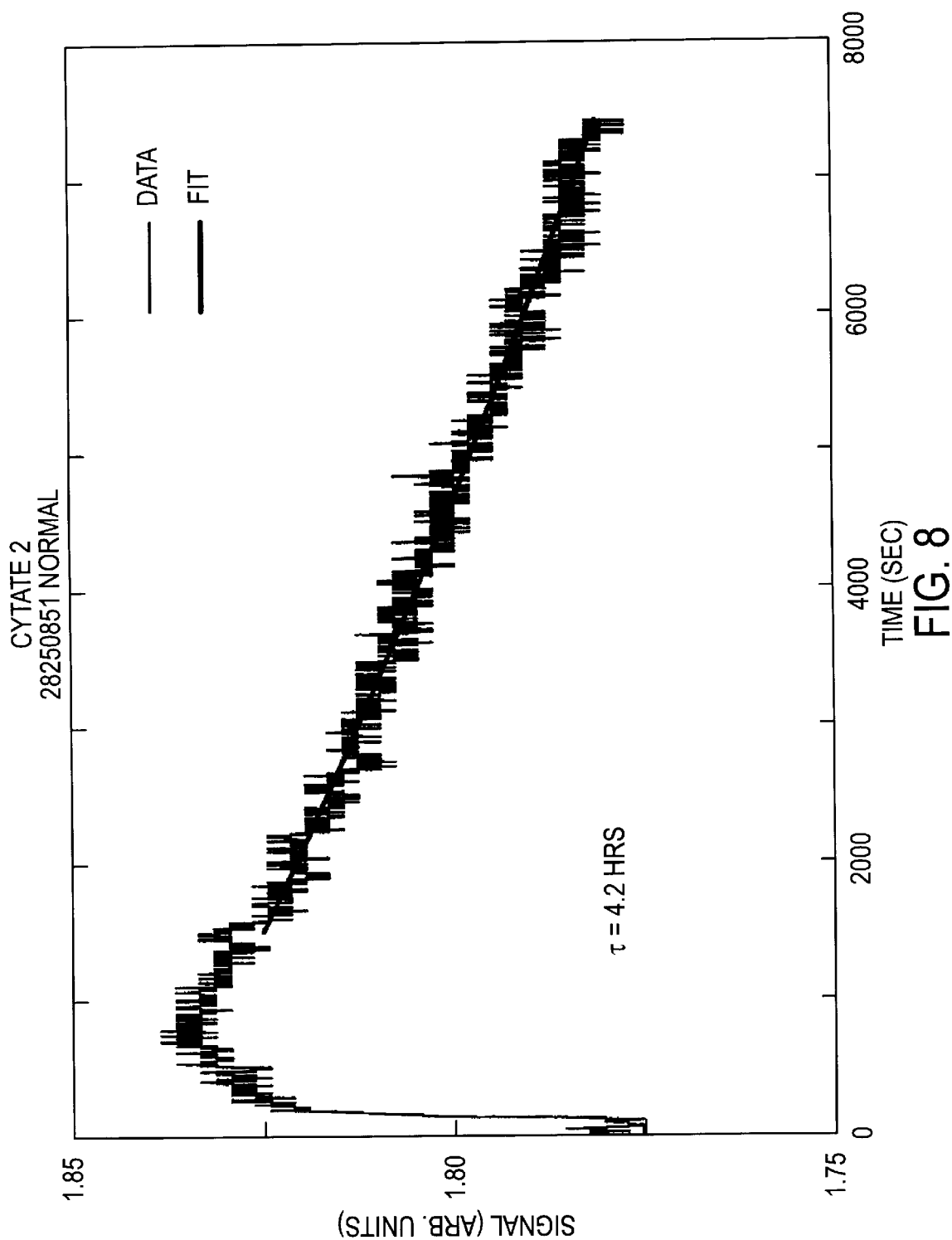
FIG. 8 is the clearance profile of Cytate 2 from the blood of a normal rat monitored at 830 nm after excitation at 780 nm.
Figure 9:
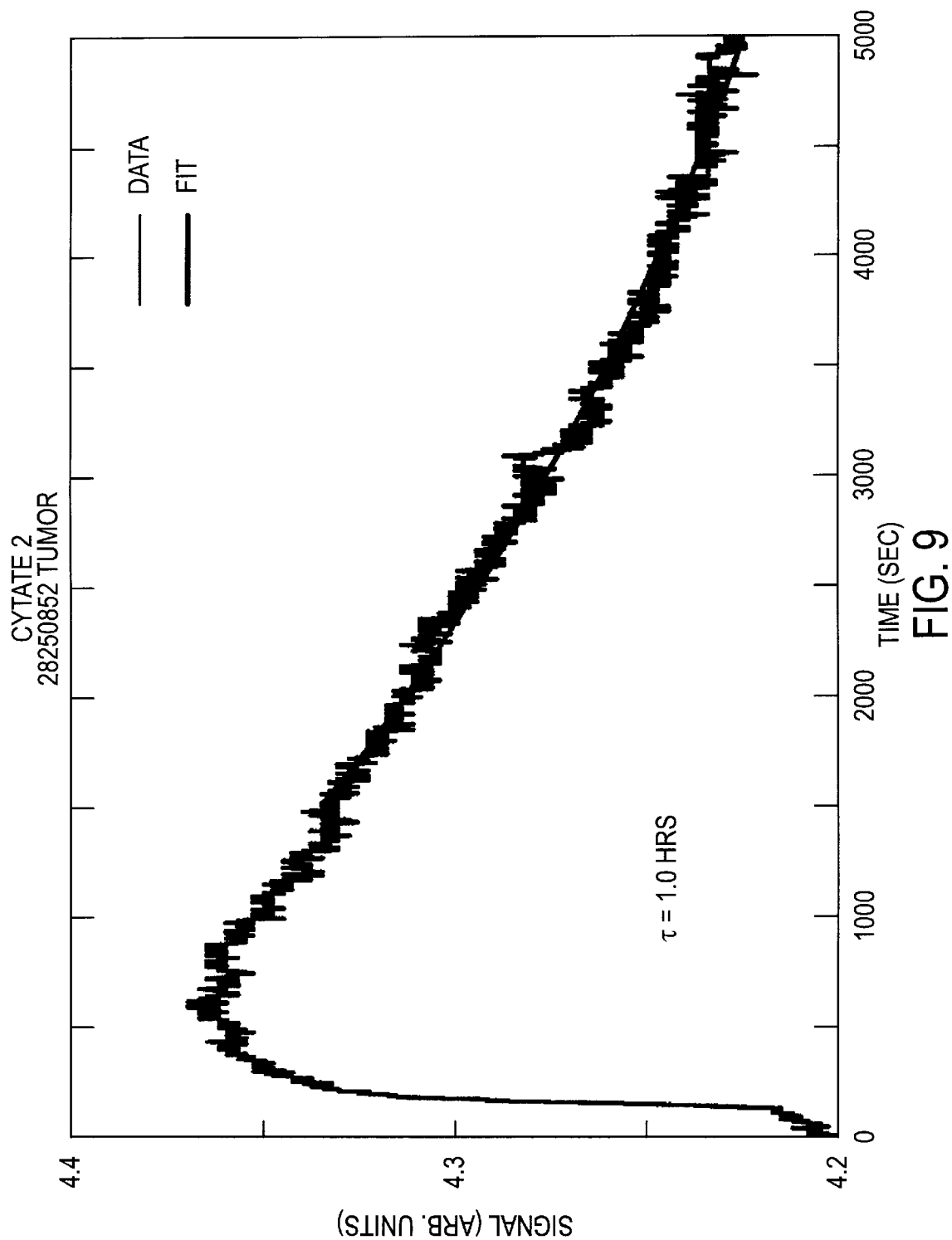
FIG. 9 is the clearance profile of Cytate 2 from the blood of a CA20948 tumored rat monitored at 830 nm after excitation at 780 nm.
Figure 10:
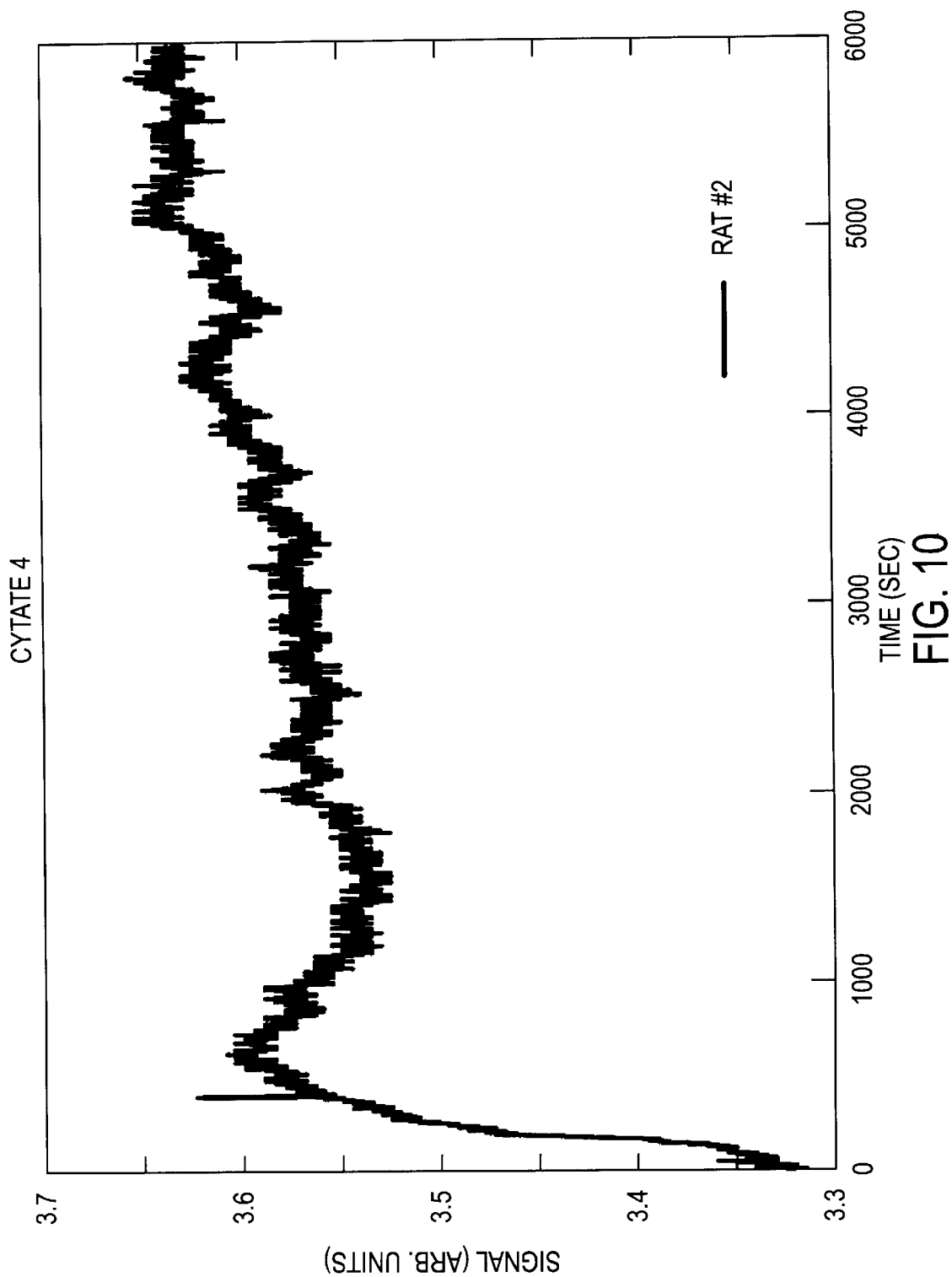
FIG. 10 is the clearance profile of Cytate 4 from the blood of a normal rat monitored at 830 nm after excitation at 780 nm.

Individual organs were removed and imaged. High uptake of the material was observed in the pancreas, adrenals and tumor tissue, while heart, muscle, spleen and liver indicated significantly less uptake (FIG. 5). This correlates very nicely with radiolabeled Octreotate in the same model system (see de Jong et al., 1998).

EXAMPLE 14

Monitoring of the blood clearance profile of peptide-dye conjugates

A laser of appropriate wavelength for excitation of the dye chromophore was directed into one end of a fiber optic bundle and the other end was positioned a few millimeters from the ear of a rat. A second fiber optic bundle was also positioned near the same ear to detect the emitted fluorescent light and the other end was directed into the optics and electronics for data collection. An interference filter (IF) in the collection optics train was used to select emitted fluorescent light of the appropriate wavelength for the dye chromophore.

Sprague-Dawley or Fischer 344 rats were used in these studies. The animals were anesthetized with urethane administered via intraperitoneal injection at a dose of 1.35 g/kg body weight. After the animals had achieved the desired plane of anesthesia, a 21 gauge butterfly with 12″ tubing was placed in the lateral tail vein of each animal and flushed with heparinized saline. The animals were placed onto a heating pad and kept warm throughout the entire study. The lobe of the left ear was affixed to a glass microscope slide to reduce movement and vibration.

Incident laser light delivered from the fiber optic was centered on the affixed ear. Data acquisition was then initiated, and a background reading of fluorescence was obtained prior to administration of the test agent. For Cytates 1 or 2, the peptide-dye conjugate was administered to the animal through a bolus injection in the lateral tail vein, typically of 0.5 to 2.0 mL. The fluorescence signal rapidly increased to a peak value. The signal then decayed as a function of time as the conjugate cleared from the bloodstream.

This procedure was repeated with several dye-peptide conjugates in normal and tumored rats and representative profiles are shown in FIGS. 6 to 10.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Becker A, Licha K, Kress M and Riefke B (1999). "Transferrin Mediated Tumor Delivery of Contrast Media for Optical Imaging and Magnetic Resonance Imaging", Biomedical Optics meeting, Jan. 23–29, 1999, San Jose, Calif.

Brinkley M (1993). "A Brief Survey of Methods for Preparing Protein Conjugates with Dyes, Haptens, and Cross-Linking Reagents", *Perspectives in Bioconjugate Chemistry* (Ed. Claude Meares, ACS Publication, Washington, D.C.), pp. 59–70.

de Jong M, et al. (1998). *Cancer Res.* 58:437–441.

Jain RK (1994). "Barriers to Drug Delivery in Solid Tumors", *Scientific American* 271:58–65.

Patonay G and Antoine MD (1991). "Near-Infrared Fluorogenic Labels: New Approach to an Old Problem", *Analytical Chemistry*, 63:321A-327A and references therein.

Slavik J (1994). *Fluorescent Probes in Cellular and Molecular Biology* (CRC Press, Inc.).

Patents and Published Patent Applications Lee LG and Woo SL. "N-Heteroaromatic ion and iminium ion substituted cyanine dyes for use as fluorescence labels", U.S. Pat. No. 5,453,505.

Hohenschuh E, et al. "Light imaging contrast agents", WO 98/48846.

Turner J, et al. "Optical diagnostic agents for diagnosis of neurodegenerative diseases by means of near infra-red radiation (NIR radiation)", WO 98/22146.

Licha K, et al. "In-vivo diagnostic process by near infrared radiation", WO 96/17628.

Snow RA, et al., "Compounds", WO 98/48838.

What is claimed is:

1. A composition comprising a cyanine dye bioconjugate of formula,

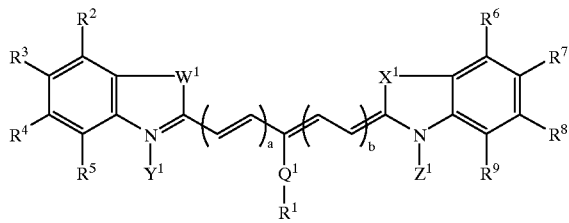

wherein a and b are independently any value from 0 to 5; $W^1$ and $X^1$ are the same or different and are selected from the group consisting of —$CR^{10}R^{11}$; $Q^1$ is a single bond or is selected from the group consisting of —O—, —S—, —Se—, and —$NR^{13}$; $R^1$, $R^{10}$, $R^{11}$, $R^{13}$, $R^{31}$–$R^{34}$, $R^{36}$–$R^{38}$ and $R^{40}$ are the same or different from the group consisting of hydrogen, $C_1$–$C_{10}$ alkyl, $C_1$–$C_{10}$ alkoxyl, $C_1$–$C_{10}$ polyalkoxyalkyl, —$CH_2(CH_2OCH_2)_c$—$CH_2$—OH, $C_1$–$C_{20}$ polyhydroxyalkyl, $C_1$–$C_{10}$ aminoalkyl, —$(CH_2)_d$—$CO_2H$, —$(CH_2)_e$—CONH-Bm, —$CH_2$—$(CH_2OCH_2)_f$—$CH_2$—CONH-Bm, —$(CH_2)_g$—NHCO-Bm, —$CH_2$—$(CH_2OCH_2)_h$ —$CH_2$—NHCO-Bm, —$(CH_2)_{yy}$—OH or —$CH_2$—$(CH_2OCH_2)_{zz}$—$CH_2$—OH; $Y^1$ is selected from the group consisting of —$CH_2$—$(CH_2OCH_2)_f$—$CH_2$—CONH-Bm, —$CH_2$—$(CH_2OCH_2)_f$—$CH_2$—NHCO-Bm, —$CH_2$—$(CH_2OCH_2)_{ee}$—$CH_2$—$N(R^{31})$—$(CH_2)_{ff}$—CONH-Bm, —$CH_2$—$(CH_2OCH_2)_{gg}$—$CH_2$—$N(R^{32})$—$(CH_2)_{hh}$—NHCO-Bm, —$CH_2$—$(CH_2OCH_2)_{ii}$—$CH_2$—$N(R^{33})$—$CH_2$—$(CH_2OCH_2)_{jj}$—$CH_2$—CONH-Bm or —$CH_2$—$(CH_2OCH_2)_{kk}$—$CH_2$—$N(R^{34})$—$CH_2$—$(CH_2OCH_2)_{ll}$—$CH_2$—NHCO-Bm; d, e, g, i, k, m, n, p, aa, bb, cc, ff, hh and yy are independently any value from 1 to 10; c, f, h, j, l, q, dd, ee, gg, ii, jj, kk, ll and zz are independently any value from 1 to 100; Bm is octreotate; $Z^1$ is selected from the group consisting of —$CH_2$—$(CH_2OCH_2)_s$—$CH_2$—$CO_2H$, —$CH_2$—$(CH_2OCH_2)_s$—$CH_2$—OH, —$CH_2$—$(CH_2OCH_2)_s$—$CH_2$—$NH_2$, —$CH_2$—$(CH_2OCH_2)_u$—$CH_2$—CONH-Dm, —$CH_2$—$(CH_2OCH_2)_o$—$CH_2$—NHCO-Dm, —$CH_2$—$(CH_2OCH_2)_{ww}$—$CH_2$—$N(R^{40})$—$(CH_2)_{xx}$—CONH-Dm, —$CH_2$—$(CH_2OCH_2)_{oo}$—$CH_2$—$N(R^{36})$—$(CH_2)_{pp}$—NHCO-Dm, —$CH_2$—$(CH_2OCH_2)_{qq}$—$CH_2$—$N(R^{37})$—$CH_2$—$(CH_2OCH_2)_{rr}$—$CH_2$—CONH-Dm or —$CH_2$—$(CH_2OCH_2)_{ss}$—$CH_2$—$N(R^{38})$—$CH_2$—$(CH_2OCH_2)_{tt}$—$CH_2$—NHCO-Dm; r, t, v, w, x, y, mm, nn, pp, uu and xx are independently any value from 1 to 10, and o, s, u, z, oo, qq, rr, ss, tt, vv and ww are independently any value from 1 to 100; and Dm is octreotate; $R^2$ to $R^9$ are the same or different and are selected from the group consisting of hydrogen, $C_1$–$C_{10}$ alkyl, $C_1$–$C_{10}$ aryl, hydroxyl, $C_1$–$C_{10}$ polyhydroxyalkyl, $C_1$–$C_{10}$ alkoxyl, amino, $C_1$–$C_{10}$ aminoalkyl, cyano, nitro, or halogen; wherein said composition further comprises a pharmaceutically acceptable carrier or excipient.

2. The composition of claim 1 wherein a and b are 3; $Q^1$ is a single bond; $R^1$ to $R^9$ are hydrogens; $W^1$ and $X^1$ are —$C(CH_3)_2$; $Y^1$ is —$CH_2$—$(CH_2OCH_2)_r$—$CH_2$—CONH-Bm; and $Z^1$ is —$CH_2$—$(CH_2OCH_2)_s$—$CH_2$—$CO_2H$ or —$CH_2$—$(CH_2OCH_2)_u$—$CH_2$—CONH-Dm, wherein r and t are independently any value from 1–4.

3. A method of performing a diagnostic or therapeutic procedure which comprises administering to an individual an effective amount of the composition of claim 1.

4. A method of performing a diagnostic or therapeutic procedure which comprises administering to an individual an effective amount of the composition of claim 2.

5. The method according to claim 3 or claim 4 wherein said diagnostic or therapeutic procedure utilizes light of wavelength in the region of 350–1300 nm.

6. The method according to claim 3 or claim 4 wherein said diagnostic procedure is optical tomography.

7. The method according to claim 3 or claim 4 wherein said diagnostic procedure is fluorescence endoscopy.

8. The method according to claim 3 or claim 4 further comprising monitoring a blood clearance profile of said bioconjugate invasively or non-invasively by fluorescence, absorbance or light scattering wherein light of wavelength in the region of 350–1300 nm is utilized.

9. The method according to claim 3 or claim 4 further comprising a step of imaging or therapy wherein said step of imaging or therapy is selected from an absorption, light scattering, photoacoustic, or sonofluorescence technique.

10. The method according to claim 3 or claim 4 wherein said procedure comprises diagnosing atherosclerotic plaques or blood clots.

11. The method according to claim 3 or claim 4 wherein said procedure comprises administering localized therapy.

12. The method according to claim 3 or claim 4 wherein said therapeutic procedure comprises photodynamic therapy.

13. The method according to claim 3 or claim 4 wherein said therapeutic procedure comprises laser assisted guided surgery (LAGS) for detection of small micrometastases.

* * * * *

SEQUENCE LISTING

<160> NUMBER OF SEQ ID NOS: 8

<210> SEQ ID NO: 1
<211> LENGTH: 8
<212> TYPE: PRT
<213> ORGANISM: Artificial Sequence
<220> FEATURE:

```
<221> NAME/KEY: SITE
<222> LOCATION: (1)
<223> OTHER INFORMATION: This is D-phenylalanine.
<220> FEATURE:
<221> NAME/KEY: DISULFID
<222> LOCATION: (2)..(7)
<220> FEATURE:
<221> NAME/KEY: SITE
<222> LOCATION: (4)
<223> OTHER INFORMATION: This is D-tryptophan.
<220> FEATURE:
<223> OTHER INFORMATION: Description of Artificial Sequence:Octreotate.

<400> SEQUENCE: 1

Phe Cys Tyr Trp Lys Thr Cys Thr
 1               5

<210> SEQ ID NO: 2
<211> LENGTH: 8
<212> TYPE: PRT
<213> ORGANISM: Artificial Sequence
<220> FEATURE:
<221> NAME/KEY: SITE
<222> LOCATION: (1)
<223> OTHER INFORMATION: This is D-phenylalanine.
<220> FEATURE:
<221> NAME/KEY: DISULFID
<222> LOCATION: (2)..(7)
<220> FEATURE:
<221> NAME/KEY: SITE
<222> LOCATION: (4)
<223> OTHER INFORMATION: This is D-tryptophan.
<220> FEATURE:
<221> NAME/KEY: SITE
<222> LOCATION: (8)
<223> OTHER INFORMATION: This C-terminal residue has had the terminal
      COOH reduced to CH2OH.
<220> FEATURE:
<223> OTHER INFORMATION: Description of Artificial Sequence:Octreotide.

<400> SEQUENCE: 2

Phe Cys Tyr Trp Lys Thr Cys Thr
 1               5

<210> SEQ ID NO: 3
<211> LENGTH: 11
<212> TYPE: PRT
<213> ORGANISM: Artificial Sequence
<220> FEATURE:
<221> NAME/KEY: SITE
<222> LOCATION: (11)
<223> OTHER INFORMATION: This C-terminal amino acid ends with an amide.
<220> FEATURE:
<223> OTHER INFORMATION: Description of Artificial Sequence:Analog of
      bombesin.

<400> SEQUENCE: 3

Gly Ser Gly Gln Trp Ala Val Gly His Leu Met
 1               5                  10

<210> SEQ ID NO: 4
<211> LENGTH: 11
<212> TYPE: PRT
<213> ORGANISM: Artificial Sequence
<220> FEATURE:
<221> NAME/KEY: SITE
<222> LOCATION: (11)
<223> OTHER INFORMATION: This C-terminal residue ends with an amide.
<220> FEATURE:
<223> OTHER INFORMATION: Description of Artificial Sequence:Analog of
      bombesin.

<400> SEQUENCE: 4
```

```
Gly Asp Gly Gln Trp Ala Val Gly His Leu Met
 1               5                  10
```

<210> SEQ ID NO: 5
<211> LENGTH: 8
<212> TYPE: PRT
<213> ORGANISM: Artificial Sequence
<220> FEATURE:
<221> NAME/KEY: SITE
<222> LOCATION: (8)
<223> OTHER INFORMATION: This C-terminal residue ends with an amide.
<220> FEATURE:
<223> OTHER INFORMATION: Description of Artificial Sequence:Analog of
      cholecystokinin.

<400> SEQUENCE: 5

```
Asp Tyr Met Gly Trp Met Asp Phe
 1               5
```

<210> SEQ ID NO: 6
<211> LENGTH: 8
<212> TYPE: PRT
<213> ORGANISM: Artificial Sequence
<220> FEATURE:
<221> NAME/KEY: MOD_RES
<222> LOCATION: (3)
<223> OTHER INFORMATION: Nle
<220> FEATURE:
<221> NAME/KEY: MOD_RES
<222> LOCATION: (6)
<223> OTHER INFORMATION: Nle
<220> FEATURE:
<221> NAME/KEY: SITE
<222> LOCATION: (8)
<223> OTHER INFORMATION: This C-terminal residue ends with an amide.
<220> FEATURE:
<223> OTHER INFORMATION: Description of Artificial Sequence:Analog of
      cholecystokinin.

<400> SEQUENCE: 6

```
Asp Tyr Xaa Gly Trp Xaa Asp Phe
 1               5
```

<210> SEQ ID NO: 7
<211> LENGTH: 8
<212> TYPE: PRT
<213> ORGANISM: Artificial Sequence
<220> FEATURE:
<221> NAME/KEY: SITE
<222> LOCATION: (1)
<223> OTHER INFORMATION: This is D-aspartic acid.
<220> FEATURE:
<221> NAME/KEY: MOD_RES
<222> LOCATION: (3)
<223> OTHER INFORMATION: Nle
<220> FEATURE:
<221> NAME/KEY: MOD_RES
<222> LOCATION: (6)
<223> OTHER INFORMATION: Nle
<220> FEATURE:
<221> NAME/KEY: SITE
<222> LOCATION: (8)
<223> OTHER INFORMATION: This C-terminal residue ends with an amide.
<220> FEATURE:
<223> OTHER INFORMATION: Description of Artificial Sequence:Analog of
      cholecystokinin.

<400> SEQUENCE: 7

```
Asp Tyr Xaa Gly Trp Xaa Asp Phe
 1               5
```

-continued

```
<210> SEQ ID NO: 8
<211> LENGTH: 8
<212> TYPE: PRT
<213> ORGANISM: Artificial Sequence
<220> FEATURE:
<221> NAME/KEY: SITE
<222> LOCATION: (1)
<223> OTHER INFORMATION: This is D-lysine.
<220> FEATURE:
<223> OTHER INFORMATION: Description of Artificial Sequence:Analog of
      neurotensin.

<400> SEQUENCE: 8

Lys Pro Arg Arg Pro Tyr Ile Leu
  1               5
```